(12) United States Patent
Stahl

(10) Patent No.: US 8,143,315 B2
(45) Date of Patent: Mar. 27, 2012

(54) SALTS OF THE ACTIVE SUBSTANCE RASAGILINE

(75) Inventor: Heinrich P. Stahl, Freiburg (DE)

(73) Assignee: Ratiopharm GmbH, Ulm (DE)

( * ) Notice: Subject to any disclaimer, the term of this patent is extended or adjusted under 35 U.S.C. 154(b) by 409 days.

(21) Appl. No.: 12/377,879

(22) PCT Filed: Aug. 17, 2007

(86) PCT No.: PCT/EP2007/007296
§ 371 (c)(1),
(2), (4) Date: Feb. 18, 2009

(87) PCT Pub. No.: WO2008/019871
PCT Pub. Date: Feb. 21, 2008

(65) Prior Publication Data
US 2010/0234636 A1  Sep. 16, 2010

(30) Foreign Application Priority Data
Aug. 18, 2006 (EP) ..................... 06017286

(51) Int. Cl.
*A01N 33/02* (2006.01)
(52) U.S. Cl. ........ 514/657; 514/308; 514/567; 514/647; 564/308; 564/428
(58) Field of Classification Search ........................ None
See application file for complete search history.

(56) References Cited

U.S. PATENT DOCUMENTS

| | | | |
|---|---|---|---|
| 5,387,612 A | 2/1995 | Youdim et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,668,181 A | 9/1997 | Youdim et al. |
| 5,744,500 A | 4/1998 | Youdim et al. |
| 5,786,390 A | 7/1998 | Youdim et al. |
| 5,891,923 A | 4/1999 | Youdim et al. |
| 6,126,968 A | 10/2000 | Peskin et al. |
| 6,277,886 B1 | 8/2001 | Levy et al. |
| 6,316,504 B1 | 11/2001 | Youdim et al. |
| 6,462,222 B1 | 10/2002 | Chorev et al. |
| 6,630,514 B2 | 10/2003 | Youdim et al. |
| 6,956,060 B2 | 10/2005 | Youdim et al. |
| 7,396,860 B2 | 7/2008 | Blaugrund et al. |
| 7,491,847 B2 | 2/2009 | Frenkel |
| 7,547,806 B2 | 6/2009 | Frenkel et al. |
| 7,572,834 B1 | 8/2009 | Sterling et al. |
| 7,598,420 B1 | 10/2009 | Sterling et al. |
| 7,619,117 B1 | 11/2009 | Sterling et al. |
| 7,750,051 B2 | 7/2010 | Frenkel et al. |
| 7,815,942 B2 | 10/2010 | Peskin |
| 7,855,233 B2 | 12/2010 | Frenkel et al. |
| 2006/0018957 A1 | 1/2006 | Lerner et al. |
| 2006/0094783 A1 | 5/2006 | Youdim |
| 2007/0100001 A1 | 5/2007 | Youdim |
| 2007/0232700 A1 | 10/2007 | Blaugrund et al. |
| 2009/0062400 A1 | 3/2009 | Oron et al. |
| 2009/0076160 A1 | 3/2009 | Lendvai et al. |
| 2009/0111892 A1 | 4/2009 | Patashnik et al. |
| 2009/0181086 A1 | 7/2009 | Safadi et al. |
| 2009/0312436 A1 | 12/2009 | Levy et al. |
| 2009/0318564 A1 | 12/2009 | Frenkel et al. |
| 2010/0008983 A1 | 1/2010 | Safadi et al. |
| 2010/0010095 A1 | 1/2010 | Frenkel |
| 2010/0137447 A1 | 6/2010 | Lehmann et al. |
| 2010/0144887 A1 | 6/2010 | Frenkel et al. |
| 2010/0145101 A1 | 6/2010 | Frenkel et al. |
| 2010/0168239 A1 | 7/2010 | Poewe |
| 2010/0189787 A1 | 7/2010 | Safadi et al. |
| 2010/0189788 A1 | 7/2010 | Safadi et al. |
| 2010/0189790 A1 | 7/2010 | Safadi et al. |
| 2010/0189791 A1 | 7/2010 | Safadi et al. |
| 2011/0130466 A1 | 6/2011 | Lorenzl |
| 2011/0152381 A1 | 6/2011 | Frenkel et al. |

FOREIGN PATENT DOCUMENTS

| | | |
|---|---|---|
| EP | 2054048 B1 | 7/2010 |
| WO | WO 95/11016 | 4/1995 |
| WO | WO 2011-003938 | 1/2011 |

OTHER PUBLICATIONS

Berge et al (J.Pharm.Salts, 1977, vol. 66, No. 1, 1-19).*
Gould, P.L. "Salt Selection for Basic Drugs", International Journal of Pharmaceutics, vol. 33(1/3), pp. 201-217 (1986).
U.S. Appl. No. 12/283,107, filed Sep. 8, 2008.
U.S. Appl. No. 13/140,402, filed Jun. 16, 2011 (Rimkus et al.).
Written Opinion of the International Searching Authority issued Feb. 18, 2009 in connection with PCT International Application No. PCT/EP2007/007296, filed Aug. 17, 2007.
PCT International Search Report issued Mar. 7, 2008 in connection with PCT International Application No. PCT/EP2007/007296. filed Aug. 17, 2007 with English translation provided by WIPO.
Gould P L, "Salt Selection for Basic Drugs", Intl J of Pharmaceutics, Elsevier BV, NL Lnkd-DOI:10.1016/0378-5173(86)90055-4, vol. 33, No. 1/03, Jan. 1, 1986 pp. 201-217.

* cited by examiner

*Primary Examiner* — Sudhakar Katakam
(74) *Attorney, Agent, or Firm* — John P. White; Cooper & Dunham LLP

(57) ABSTRACT

The invention relates to novel salts of the active substance rasagiline. The salts show excellent processability even after prolonged storage and an excellent storage stability usually superior to known salts after being processed into tablets.

7 Claims, 2 Drawing Sheets

SALTS OF THE ACTIVE SUBSTANCE RASAGILINE

This application corresponds to the national phase of International Application No. PCT/EP07/007,296, filed Aug. 17, 2007, which, in turn, claims priority to European Patent Application No. 06.017286.3, filed Aug. 18, 2006, the contents of both of which are incorporated by reference herein in their entirety.

The invention relates to novel salts of the active substance rasagiline. Even after prolonged storage, the salts show excellent processability and, after being processed into tablets, have excellent storage stability usually superior to known salts.

Rasagiline, the R(+) enantiomer of n-propargyl-1-aminoindane, is an active substance which is known for a long time and is used in particular to treat Parkinson's disease, dementia and Alzheimer's disease. Further indications are described in EP-A 436 492 and WO 95/11016, for example, to which express reference is made in this respect. The compound is already comprised by the disclosure of DE 1 443 559 and DE 1 443 403. Rasagiline is described as an individual compound in EP-A 436 492 disclosing rasagiline and in general pharmaceutically compatible acid additions salts thereof, in particular the hydrochloride and the tartrate of rasagiline. Further rasagiline salts are described in WO 95/11016, namely the sulfate, phosphate, mesylate (methane sulfonate), maleate, esylate (ethane sulfonate), acetate, fumarate, hydrobromide, tosylate (toluene sulfonate) and benzoate.

The known salts accumulate as a white crystal powder yet are disadvantageous, in particular after prolonged storage. For example, the tartrate of rasagiline already includes undesired agglomerates which complicate processing immediately after the production thereof. The mesylate, hydrochloride and phosphate of rasagiline show such agglomerates after storage even in a closed glass bottle and can also display a slight discoloration. When stored under humid conditions (40° C., 75% relative humidity in an open glass bottle), a sticky powder which is difficult to process forms from the mesylate, the hydrochloride and the phosphate salt of rasagiline. Agglomerates interfere with the processing of the active substance, in particular with the processing into solid medicinal products, since they may result in inhomogeneities in the medicinal product. Difficulties also occur above all in the production of tablets by direct compression when the active substance is partially agglomerated.

Although the known rasagiline salts are largely storage-stable in solid medicinal products, a certain decomposition of the active substance still occurs. In addition, many salts display an undesired hygroscopicity.

Technology needs salts of rasagiline which have improved storage stability and thus can be processed well even after prolonged storage. In solid medicinal product formulations, the salts shall at least be as chemically stable as the known salts, preferably have a greater stability and the least possible hygroscopicity.

Correspondingly, rasagiline salts are provided according to the invention with an acid of general formula I

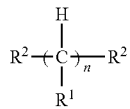

wherein the residues $R^1$ independently represent a hydrogen atom or a $C_1$-$C_4$ alkyl residue, $R^2$ is a COOH group or an $S(O)_m H$ group, n is an integer ranging from 0 to 4 and m has the value 2, 3 or 4.

According to the invention it is preferred for residues $R^1$ to be independently hydrogen atoms or methyl groups, most preferably all residues $R^1$ are hydrogen atoms. According to the invention, the index m is preferably 3 and therefore the rasagiline salt is preferably a disulfonate salt according to the invention. The index n is preferably 0 or 2. When $R^2$ is an $S(O)_m H$ group, n is preferably not 0. The rasagiline oxalate and the rasagiline edisilate (=rasagiline ethane disulfonate, salt of the ethane disulfonic acid) are particularly preferred according to the invention and the rasagiline edisilate is most preferred according to the invention.

According to the invention the salts of rasagiline can be monosalts or disalts or mixtures of monosalts and disalts, i.e. one or both acid groups of the diacids according to the invention form a salt with a rasagiline molecule. If free acid groups are available, they may form salts, where appropriate, with further conventional pharmaceutically compatible counterions, such as sodium, potassium, etc., or be available as free acid groups. However, the dicarboxylic acid salts and the disulfonic acid salts of rasagiline are preferred according to the invention.

It has surprisingly been found that the rasagiline salts, in particular the rasagiline oxalate and the rasagiline edisilate, are available as a white crystal powder which is free of agglomerates and does not form any agglomerates even after long storage. This applies above all to dry storage and in particular in the case of the rasagiline edisilate also to storage under humid conditions. This enables easier processing of the rasagiline salts according to the invention, above all also in the production of solid medicinal products, such as tablets, and above all in the production of tablets by direct tabletting.

Thus, the invention also relates to tablets which are produced by direct tabletting, and also to granules and tablets which are produced by a common granulation method or by compacting.

Another advantage of the rasagiline salts according to the invention is their markedly different solubility. Thus, the rasagiline edisilate dissolves very rapidly and well, thus rendering it particularly favorable for the formulation of fast-releasing, solid drug dosage forms, in particular of fast-releasing tablets. On the other hand, e.g. the rasagiline oxalate is much more difficult to dissolve so that the rasagiline oxalate can preferably be used for slow-releasing or delayed-releasing medicinal products. According to the invention the medicinal products containing the novel rasagiline salts can be fast-releasing and delayed-releasing medicinal products or medicinal products slowing release. Fast-releasing medicinal products are preferred.

The rasagiline salts according to the invention can be produced e.g. by dissolving or suspending the rasagiline base in a suitable solvent and mixing it with a solution or suspension of the corresponding diacid. When allowed to stand and, where appropriate, to cool, the rasagiline salt precipitates which can then be further processed as usual. Suitable solvents are e.g. organic solvents or solvent mixtures in which the acid is soluble and the rasagiline is soluble and the rasagiline salt is insoluble, or solvents in which either the acid or the rasagiline is insoluble and the rasagiline salt is soluble at elevated temperature and insoluble at low temperature. Suitable solvents are e.g. polarprotic solvents, such as alcohols, in particular $C_1$-$C_8$ alkanols, such as $C_1$-$C_4$ alkanols, 2-propanol being particularly preferred. As a result of these methods, the salts accumulate as crystals.

If rasagiline salts are produced in the above way, they accumulate in a very finely divided form and with a small size distribution. In particular the rasagiline edisilate preferred according to the invention accumulates in a very finely divided form. In the thus produced salts, in particular the rasagiline edisilate according to the invention and the rasagiline oxalate according to the invention, and also the known rasagiline salts not according to the invention, such as the rasagiline tartrate and the rasagiline mesylate, the fraction of the particles having a size of 250 μm or below is usually over 90%, preferably over 95%. Preferred particle size distributions for the salts according to the invention and also for the tartrates and mesylates not according to the invention, are as follows:

| d(0.1) [μm] | d(0.5) [μm] | d(0.9) [μm] | |
|---|---|---|---|
| 1.0-40 | 5.0-70 | 10-200 | conventional |
| 1.5-30 | 7.5-60 | 20-180 | preferred |
| 2-25 | 10-55 | 30-170 | more preferred | the particle sizes for the edisilate and the tartrate being more closely to the lower limits and the particle sizes for the oxalate and the mesylate being more closely to the upper limits. The particle sizes are determined as described in the examples.

The rasagiline salts according to the invention can also be produced in an amorphous way, e.g. by spray-drying. The amorphous salts are also a subject matter of the invention. Crystalline salts are preferred.

The rasagiline base can be produced in known manner, e.g. as described in EP-A 436 492.

The rasagiline salts according to the invention are processed in known manner into medicinal products, in particular solid medicinal products. The medicinal products contain the rasagiline salt according to the invention in a therapeutically effective amount, i.e. in the case of a solid drug dosage form, such as a tablet, in particular in an amount of about 0.1 mg to about 1000 mg per unit dose (i.e. e.g. for one tablet), preferably in an amount of about 0.5 mg to about 10 mg per unit dose. In the case of a liquid dosage form, a medicinal product according to the invention also contains a therapeutically effective amount of the rasagiline salt according to the invention, in particular an amount of about 0.1 mg/ml to about 100 mg/ml, preferably about 0.5 mg/ml to about 10 mg/ml of the medicinal product. A preferred administered amount of the medicinal product ranges from 0.1 ml to 1.0 ml of the medicinal product per day according to the invention.

Solid dosage forms, such as pellets, granules, satchets, hard gelatin capsules, soft gelatin capsules, dragees, tablets, etc., are preferred according to the invention. Tablets which may be coated or uncoated, are particularly preferred according to the invention. The tablets can be produced by conventional granulation methods or preferably by direct compression according to the invention. The rasagiline salts according to the invention are formulated with conventional pharmaceutical excipients and additives. Suitable additives are usually fillers, binders, disintegrants, lubricants, stabilizers and flow regulators, as well as further additives, where appropriate.

The solid dosage forms preferred according to the invention, in particular the tablets according to the invention, usually contain over 50% by weight of fillers, more preferably over 65% by weight of fillers, most preferably 70 to 95% by weight of fillers.

The disintegrant content is usually 1 to 25% by weight, preferably 1 to 20% by weight, in particular 2 to 15% by weight. Suitable ranges for the disintegrant content are also e.g. 2 to 5% by weight or 15 to 20% by weight depending on the employed disintegrants, fillers and other additives.

The lubricant content is usually 0.1 to 4% by weight, preferably 0.2 to 4% by weight.

If the composition comprises a flow regulator, it is usually available in an amount of 0.5 to 5% by weight, preferably 1 to 4% by weight, in particular 2 to 3% by weight.

The stabilizer content (if available) usually ranges from 0.5 to 4% by weight, preferably 1 to 3% by weight.

The employed fillers may be one or more compounds which supply part of the material to achieve the required and desired total tablet mass. Inter alia microcrystalline cellulose can be used in various particle sizes, in particular with an average particle size ranging from 20 μm to 200 μm, in particular ranging from 50 μm to 150 μm, e.g. about 100 μm, such as the known avicel products, such as Avicel PH-101 and PH-102. Further suitable fillers are e.g. lactose, cellactose (a mixture of cellulose and lactose), calcium phosphate, dextrose, mannitol, maltodextrin, isomalt, where appropriate also sorbitol and saccharose. If direct compression is intended, attention should be paid regarding the selection of the fillers to the fact that grades are used which are suited for the direct compression of tablets. This is included in the instructions of the manufacturer of the commercial products in each case or can be checked by simple tests. The most preferred filler is microcrystalline cellulose (commercial products are e.g. Avicel, Vivapur and Emcocel).

Along with the above fillers, in particular mannitol, sorbitol and isomalt are preferred fillers as well; the filler mannitol is particularly preferred according to the invention. Here, reference can be made to the pearlitol products, for example.

According to the invention the filler is also preferably a mixture of microcrystalline cellulose and mannitol. The ratio of microcrystalline cellulose and mannitol is not particularly limited in this embodiment, however, it is preferred to use more mannitol than microcrystalline cellulose, and the ratio preferably ranges from 1:1.1 to 1:5, more preferably from 1:2 to 1:4.

Suitable disintegrants are known in the art. Disintegrants are often also designated in German by the English term "disintegrants". Disintegrants preferred according to the invention are e.g. crospovidone (collidone CL) and starch or preagglutinated starch, in particular the commercial product "Starch 1500". Further suitable starches are commercially available e.g. under the designations of Lycatab PGS, Prejel and Sepistab ST 200. Furthermore, it is also possible to use the known so called "super disintegrants", such as croscarmellose sodium (e.g. Ac-Di-Sol and others) and carboxymethyl starch sodium (e.g. Explotab, Primojel and others). Starches, such as Starch 1500, are particularly preferred.

According to the invention the composition can contain as lubricant one or more compounds which support the production and processing of the tablet. Usable lubricants are inter alia stearic acid and the derivatives thereof, such as calcium stearate, and in particular sodium stearyl fumarate (which is commercially available under the designation of Pruv, for example) and magnesium stearate, glycerolmono- glyceroldi- and in particular glyceroltristearate, hydrogenated vegetable oil (e.g. Lubritab, Dynasan, Sterotext) or a polyethylene glycol (e.g. Lutrol, Carbowax).

Where appropriate, the pharmaceutical composition according to the invention may comprise one or more flow regulators. Suitable flow regulators are magnesium trisilicate, talcum and in particular silicon dioxide (e.g. Aerosil).

The pharmaceutical compositions according to the invention may also contain stabilizers for the active substance, such as citric acid, tartaric acid, lactic acid, etc., preferably citric acid.

The pharmaceutical compositions according to the invention can contain further conventional pharmaceutically compatible additives and excipients, preferably they contain no further excipients apart from the above indicated ones (fillers, disintegrants, lubricants and, where appropriate, flow regulators and stabilizers).

Some fillers, such as microcrystalline cellulose, can also serve as binders. Therefore, fillers having binder function are also counted among the fillers within the scope of this application.

If the pharmaceutical composition according to the invention is available as a tablet, it can be film-coated with one or more coating agents. Usable coating agents are hypromellose (hydroxypropylmethyl cellulose), polyvinyl alcohol, sodium carboxymethyl cellulose and various methacrylic acid polymers (eudragits), with hypromellose and in particular eudragits being preferred. The tablets are coated as usual. In addition to the coating agent, the coating may also contain further constituents of tablet coatings, such as plasticizers, pigments, pore forming materials or suspension stabilizers, such as polyethylene glycol (PEG), talcum or titanium dioxide and, where appropriate, also lactose.

The tablet weight is not particularly limited; tablets having 100 to 600 mg, e.g. 100 to 300 mg, in particular about 200 mg, are common practice.

The following examples explain the invention. The employed rasagiline base was obtained according to the instructions of EP-A 436 492.

EXAMPLE 1

Rasagiline Edisilate 47 g rasagiline base were suspended in 668 ml 2-propanol. Then, 25.9 g ethanedisulfonic acid dissolved in 668 ml 2-propanol were added. A white solid precipitated from the meanwhile clear solution. The suspension was allowed to stand in a refrigerator for 2 days, then filtrated and subsequently washed with 100 ml cooled 2-propanol. The residue was dried in a drying cabinet at 45° C. Yield: 54.9 g (56.3% of the theoretical) white crystals; water content (Karl Fischer): about 0.1%; melting point 201° C. (clear, transparent melt); TLC: peak at 208.83° C.; $[\alpha]_D^{20}$: +40.3° (2% in $H_2O$); elemental analysis: C=58.76% (theoretical: 58.63%), H=6.16% (theoretical: 6.05%), N=5.13% (theoretical: 5.26%), S=12.22% (theoretic 12.04%).

Figure 1:
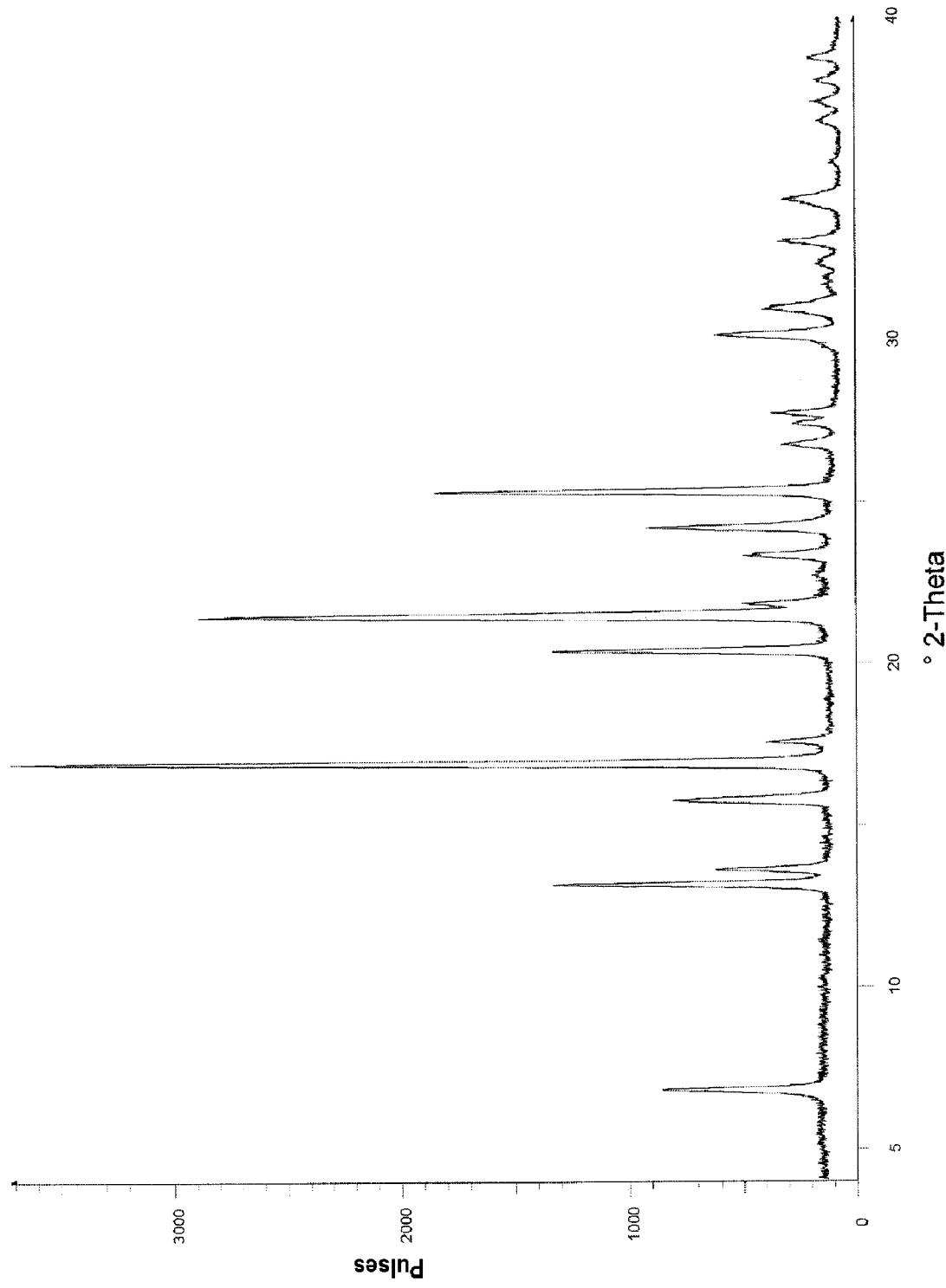
FIG. 1 shows a powder X-ray diagram of the salt prepared in Example 1.

A powder X-ray diagram of the prepared salt was made which is shown in FIG. 1. A list of the 2-theta values is as follows:

| 2-Theta | d values | I (rel) |
|---|---|---|
| 6.79° | 13.015 | 22.9 |
| 13.15° | 6.726 | 35.7 |
| 13.60° | 6.503 | 16.5 |
| 15.75° | 5.621 | 21.5 |
| 16.90° | 5.241 | 100.0 |
| 17.54° | 5.053 | 10.4 |
| 20.38° | 4.355 | 35.7 |
| 21.45° | 4.140 | 77.6 |
| 21.83° | 4.067 | 13.0 |
| 22.70° | 3.915 | 5.0 |
| 23.32° | 3.811 | 13.0 |
| 24.19° | 3.676 | 24.5 |
| 25.31° | 3.516 | 49.7 |
| 26.76° | 3.328 | 8.6 |
| 27.41° | 3.252 | 7.2 |
| 27.74° | 3.214 | 9.7 |
| 29.79° | 2.997 | 3.4 |
| 30.17° | 2.960 | 16.5 |
| 30.98° | 2.884 | 10.5 |
| 31.64° | 2.825 | 3.6 |
| 31.93° | 2.801 | 3.3 |
| 32.36° | 2.764 | 4.6 |
| 33.07° | 2.706 | 8.8 |
| 34.13° | 2.625 | 5.1 |
| 34.37° | 2.607 | 8.4 |
| 35.50° | 2.527 | 2.8 |
| 36.80° | 2.440 | 4.4 |
| 37.39° | 2.403 | 5.0 |
| 38.04° | 2.363 | 4.2 |
| 38.74° | 2.322 | 5.3 |
| 40.04° | 2.250 | 2.0 |
| 40.72° | 2.214 | 2.3 |
| 41.26° | 2.186 | 3.2 |
| 41.48° | 2.175 | 2.5 |
| 42.07° | 2.146 | 2.5 |
| 42.91° | 2.106 | 4.0 |
| 43.67° | 2.071 | 2.6 |
| 44.02° | 2.055 | 2.6 |
| 44.94° | 2.015 | 5.4 |
| 46.42° | 1.955 | 2.1 |
| 46.90° | 1.936 | 2.1 |
| 48.43° | 1.878 | 3.0 |
| 48.86° | 1.863 | 3.2 |
| 49.19° | 1.851 | 2.3 |
| 50.08° | 1.820 | 2.4 |
| 50.94° | 1.791 | 2.5 |
| 51.56° | 1.771 | 2.7 |
| 51.98° | 1.758 | 2.7 |
| 53.34° | 1.716 | 2.1 |
| 53.98° | 1.697 | 1.9 |
| 58.66° | 1.573 | 1.6 |
| 59.37° | 1.555 | 1.8 |
| 59.73° | 1.547 | 1.8 |
| 61.10° | 1.516 | 1.7 |
| 63.36° | 1.467 | 1.8 |
| 66.19° | 1.411 | 1.8 |
| 66.83° | 1.399 | 1.5 |
| 69.32° | 1.354 | 1.5 |
| 71.58° | 1.317 | 1.5 |
| 72.10° | 1.309 | 1.6 |
| 74.48° | 1.273 | 1.4 |
| 77.89° | 1.225 | 1.5 |
| 79.53° | 1.204 | 1.4 |

The 2-theta values can display a certain deviation of ±0.2°, and it is assumed that the resulting polymorphic form of the rasagiline edisilate is clearly characterized by the five most intense peaks, preferably by the seven most intense peaks, more preferably by the ten most intense peaks.

EXAMPLE 2

Rasagiline Oxalate 60 g rasagiline base were suspended in 885 ml 2-propanol. Then, 32.7 g oxalic acid dissolved in 885 ml 2-propanol were added. The mixture was allowed to stand in a refrigerator overnight, then filtrated and subsequently washed with 100 ml cooled 2-propanol. The residue was dried in a drying cabinet at 45° C. Yield: 87.6 g (93.1% of the theoretical) white crystals; water content (Karl Fischer): about 0.1%; melting point 204° C. (clear, brown melt); TFC: peak at 209.52° C.; $[\alpha]_D^{20}$: +28.9° (2% in ethanol); elemental analysis: C=64.39% (theoretical: 64.36%), H=5.91% (theoretical: 5.79%), N=5.43% (theoretical: 5.36%).

Figure 2:
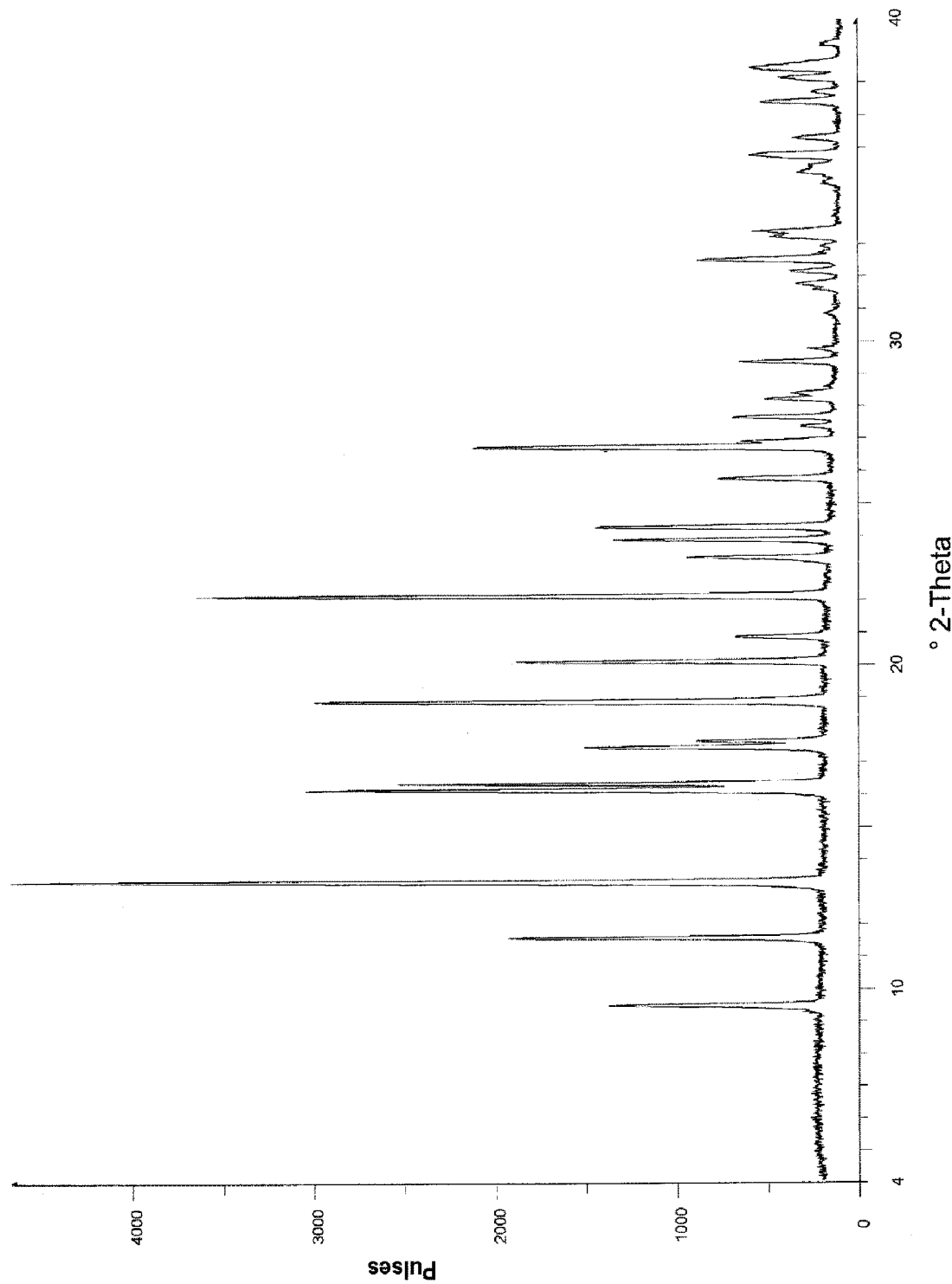
FIG. 2 shows a powder X-ray diagram of the product made in Example 2.

A powder X-ray diagram of the resulting product was made which is shown in FIG. 2. The peak list (up to a 2-theta value of 40.09) is as follows:

| 2-Theta | d values | I (rel) |
|---|---|---|
| 9.43° | 9.373 | 25.0 |
| 11.55° | 7.657 | 38.8 |
| 13.27° | 6.667 | 100.0 |
| 16.31° | 5.430 | 52.5 |
| 17.44° | 5.081 | 29.3 |
| 17.63° | 5.027 | 15.7 |
| 18.85° | 4.704 | 63.0 |
| 20.10° | 4.414 | 38.3 |
| 20.84° | 4.259 | 11.6 |
| 22.11° | 4.017 | 77.8 |
| 23.32° | 3.811 | 17.6 |
| 23.86° | 3.727 | 26.4 |
| 24.27° | 3.664 | 28.9 |
| 25.75° | 3.457 | 14.1 |
| 26.75° | 3.330 | 43.7 |
| 26.96° | 3.309 | 11.3 |
| 27.37° | 3.256 | 3.9 |
| 27.64° | 3.225 | 12.6 |
| 28.21° | 3.161 | 8.5 |
| 28.38° | 3.142 | 5.4 |
| 29.39° | 3.036 | 11.6 |
| 29.78° | 2.998 | 3.3 |
| 30.86° | 2.896 | 1.7 |
| 31.60° | 2.829 | 3.0 |
| 31.78° | 2.813 | 5.0 |
| 32.19° | 2.779 | 5.5 |
| 32.53° | 2.750 | 17.2 |
| 32.78° | 2.730 | 2.3 |
| 32.96° | 2.716 | 2.1 |
| 33.26° | 2.692 | 8.1 |
| 33.43° | 2.679 | 10.0 |
| 33.91° | 2.642 | 0.7 |
| 34.95° | 2.565 | 1.9 |
| 35.23° | 2.545 | 5.2 |
| 35.46° | 2.529 | 3.7 |
| 35.79° | 2.507 | 11.0 |
| 36.32° | 2.471 | 5.5 |
| 37.42° | 2.402 | 9.7 |
| 37.76° | 2.380 | 3.3 |
| 38.18° | 2.355 | 7.1 |
| 38.49° | 2.337 | 10.9 |
| 39.21° | 2.296 | 2.3 |
| 40.09° | 2.247 | 0.8 |

The 2-theta values may show a deviation of ±0.2°, and it is assumed that the polymorphic form of the rasagiline oxalate is clearly characterized by the five most intense peaks, preferably by the seven most intense peaks, more preferably by the ten most intense peaks and in particular by the 15 most intense peaks.

The x-ray powder diagrams were made as follows:
The measurements were made in transmission geometry.
Sample Preparation:
The sample is pestled in an agate mortar in air. The pestled substance is clamped between two films into the sample carrier.
Measurement Parameters:
Carrier films: reflex-free polyacetate film
Measurement range 2θ=4°-90°
PSD step 0.5°
Measurement time 60 s/step corresponding to 840 s per reading point
Sample rotation
Device Parameter:
Transmission diffractometer Stoe Stadi P, year of manufacture 2004
Radiation: Cu K$\alpha_1$; λ=1.5406 Å
Monochromator: upstream curved Ge(111) monochromator
Divergent aperture: 6 mm (vertical)
Short collimator with horizontal divergent aperture 1 mm
Site-sensitive detector (linear PSD; angle resolution better than 0.06° 2θ FWHM)
Generator Adjustment:
40 kV, 30 mA.

EXAMPLE 3

Determination of Solubility 0.5 g rasagiline oxalate or 3 g rasagiline edisilate were placed in a 25 ml beaker in each case containing 5 mm of the respective solvent each and were ultrasonicated. After one-hour storage at 37° C., the samples were filtrated, the filtrates were diluted and analyzed by means of HPLC. In addition, the pH of the solutions was determined.

| Salt | Solvent | pH of the saturated solution | solubility [mg/ml] |
|---|---|---|---|
| Rasagiline edisilate | 0.1 N HCl | 1.0 | 359.8 |
| | USP acetate buffer, pH 4.5 | 4.4 | 475.3 |
| | USP phosphate buffer, pH 6.8 | 6.2 | 497.7 |
| | Demineralized water | 4.4 | 342.5 |
| Rasagiline oxalate | 0.1 N HCl | 1.2 | 29.9 |
| | USP acetate buffer, pH 4.5 | 3.4 | 24.3 |
| | USP phosphate buffer, pH 6.8 | 3.4 | 24.2 |
| | Demineralized water | 2.7 | 19.7 |

EXAMPLE 4

Determination of Hygroscopicity

Rasagiline edisilate according to Example 1, rasagiline oxalate according to Example 2 and rasagiline mesylate which is present in the currently commercially available rasagiline medicinal product, were stored in humidity chambers at defined humidity and room temperature. With storage below 93% humidity, the rasagiline mesylate absorbed large amounts of water and liquefied. The rasagiline salts according to the invention showed no water absorption.

EXAMPLE 5

Stability Tests

Rasagiline edisilate and oxalate as well as mesylate, hydrochloride, phosphate and tartrate were stored under stress conditions for several weeks. The appearance, chemical purity and water content were investigated after fixed time intervals.

Storage at 60° C. in a closed glass bottle:

| Time | Edisilate | Oxalate | Mesylate | Hydrochloride | Phosphate | Tartrate |
|---|---|---|---|---|---|---|
| 0 | white, crystalline powder | white, crystalline powder | white crystalline powder | white crystalline powder | white crystalline powder | white crystalline powder with agglomerates |
| 4 weeks | unchanged | unchanged | white powder, agglomerates | white powder, agglomerates | yellow powder, agglomerates | unchanged |
| 8 weeks | unchanged | unchanged | white powder, agglomerates | white powder, agglomerates | yellow powder, agglomerates | unchanged |
| 12 weeks | unchanged | unchanged | white powder, agglomerates | white powder, agglomerates | yellow powder, agglomerates | unchanged |

Chemical purity and water content remained unchanged in all samples.

Storage at 40° C./75% relative humidity in an open glass bottle:

| Time | Edisilate | Oxalate | Mesylate | Hydrochloride | Phosphate | Tartrate |
|---|---|---|---|---|---|---|
| 0 | white crystalline powder | white crystalline powder | white crystalline powder | white crystalline powder | white crystalline powder | white crystalline powder with agglomerates |
| 4 weeks | unchanged | white powder, agglomerates | white sticky powder | white sticky powder | yellow sticky powder | unchanged |
| 8 weeks | unchanged | white powder, agglomerates | white sticky powder | white sticky powder | yellow sticky powder | unchanged |
| 12 weeks | unchanged | white powder, agglomerates | white sticky powder | white sticky powder | yellow sticky powder | unchanged |

Chemical purity and water content remained unchanged in all samples with the exception of phosphate. In the case of rasagiline phosphate, the water content increased from 0.1% ($t_0$) via 0.2% (4 weeks) to 0.4% (8 weeks) and the total content of chemical contaminations increased from 0.0% ($t_0$) via 0.05% (4 weeks) to 0.19% (8 weeks). The values after 12 weeks of storage were no longer determined for rasagiline phosphate.

EXAMPLE 6

Formulations

According to the following Table, tablets were produced using different rasagiline salts by two different granulation methods and by a direct compression method:

| | Formulations | | | |
|---|---|---|---|---|
| | Granulation 1 with mannitol | | Granulation 2 and direct compression without mannitol | |
| Composition | [mg] | [%] | [mg] | [%] |
| Rasagiline (as different salts) API | 1 | 0.50 | 1 | 0.50 |
| Mannitol (Pearlitol 160 C) filler | 109.00 | 54.23 | — | — |
| Avicel PH 101 filler | 75.80 | 37.71 | 184.8 | 91.94 |
| Starch 1500 (preagglutinated corn starch) distintegrant | 10.00 | 4.98 | 10.00 | 4.98 |
| Aerosil R972 (colloidal, anhydrous silica) disintegrant | 1.20 | 0.60 | 1.20 | 0.60 |
| Citric acid stabilizer | 2.00 | 1.00 | 2.00 | 1.00 |
| Magnesium stearate lubricant | 2.00 | 1.00 | 2.00 | 1.00 |
| Total | 201.0 | 100.00 | 201.0 | 100.00 |

1. Wet Granulation (1000 Tablets)
    1. dissolving 2 g citric acid and rasagiline salt in 40 g demineralized water in a 100 ml beaker
    2. adding 109 g mannitol (Pearlitol 160 C), 35 g Avicel PH 101 (part 1) and 10 g Starch 1500 to the Diosna P1 (granulator-shredder 1500 rpm, rotor 500 rpm) followed by 3 minutes of mixing
    3. 2 minutes of granulating the mixture (item 2) with granulation solution (item 1) in the Diosna P1 (shredder 1500 rpm, rotor 500 rpm)
    4. granulating the mixture (item 3) in the Diosna P1 for another 2 minutes
    5. screening the granules through a 2 mm manual screen
    6. drying the granules at room temperature overnight
    7. screening the dry granules through a 0.3 mm manual screen and filling them into a brown 1 liter glass 8. adding 40.8 g Avicel PH 101 (part 2) and 1.2 g Aerosil R972 into the brown glass followed by mixing in a Turbula mixer (30 rpm) for 10 minutes
9. adding 2 g magnesium stearate to the mixture followed by mixing in the Turbula (30 rpm) for 3 minutes
10. compressing the tablets with an 8 mm die using an eccentric press (Korsch EKO)

2. Wet Granulation (1000 Tablets)
   1. dissolving 2 g citric acid and rasagiline salt in 40 g demineralized water in a 100 ml beaker
   2. adding 92.4 g Avicel PH 101 (part 1) and 10 g Starch 1500 to the Diosna P1 (granulator-shredder 1500 rpm, rotor 500 rpm) followed by 3 minutes of mixing
   3. 2 minutes of granulating the mixture (item 2) with a granulation solution (item 1) in the Diosna P1 (shredder 1500 rpm, rotor 500 rpm)
   4. granulating the mixture (item 3) in the Diosna P1 for another 2 minutes
   5. screening the granules through a 2 mm manual screen
   6. drying the granules at room temperature overnight
   7. screening the dry granules through a 0.3 mm manual screen and filling them into a brown 1 liter glass
   8. adding 92.4 g Avicel PH 101 (part 2) and 1.2 g Aerosil R972 to the brown glass followed by 10 minutes of mixing in a Turbula mixer (30 rpm)
   9. adding 2 g magnesium stearate to the mixture followed by 3 minutes of mixing in the Turbula (30 rpm)
   10. compressing the tablets with an 8 mm die using an eccentric press (Korsch EKO)

3. Direct Compression (1000 Tablets)
   1. adding rasagiline salt, 2 g citric acid (micronized) and 20 g Avicel PH 101 (part 1) to a brown 500 ml glass followed by 5 minutes of mixing with a Turbula mixer (30 rpm)
   2. screening the mixture (item 1) through a 0.5 mm manual screen
   3. adding 10 g Starch 1500 and 70 g Avicel PH 101 (part 2) to the mixture (item 2) followed by 5 minutes of mixing in a Turbula mixer (30 rpm)
   4. filling the mixture from item 3 into a brown 1 liter glass and adding 94.8 g Avicel PH 101 (part 3) to the brown glass followed by 5 minutes of mixing in a Turbula mixer (30 rpm)
   5. adding 1.2 g Aerosil R972 to the brown glass followed by 5 minutes of mixing in a Turbula mixer (30 rpm)
   6. screening the powder through a 0.5 mm manual screen followed by 5 minutes of mixing in a Turbula mixer (30 rpm)
   7. adding 2 g magnesium stearate to the mixture followed by 5 minutes of mixing in a Turbula mixer (30 rpm)
   8. compressing the tablets with an 8 mm die using an eccentric press (Korsch EKO)

The results of the different tablettings are shown in the following table:

Results of tabletting

| Formulation | Parameter | Rasagiline mesylate | Rasagiline hydrochloride | Rasagiline ethane disulfonate | Rasagiline phosphate | Rasagiline tartrate |
|---|---|---|---|---|---|---|
| Granulation 1 with mannitol (55%) | tablet weight | 201.1 mg | 199.7 mg | 201.0 mg | 205.3 mg | 203.7 mg |
| | Solubility in citric acid solution | very high | very high | very high | high | high |
| | hardness at 8 kN pressing force | 54 N | 44 N | 57 N | 60 N | 61 N |
| Granulation 2 without mannitol | tablet weight | 200.4 mg | 197.0 mg | 201.4 mg | 203.4 mg | 201.7 mg |
| | solubility in citric acid solution | very high | very high | very high | high | high |
| | pressing force/ hardness | 2.7 kN/77.1 N | 2.7 kN/61.8 N | 2.8 kN/77.7 N | 2.8 kN/75.2 N | 2.7 kN/65.6 N |
| Direct compression without mannitol | tablet weight | 201.3 mg | 199.8 mg | 201.0 mg | 201.0 mg | 201.0 mg |
| | hardness/ RSD at 2.7 kN compressive force | 77 N/4.10% | 74.4 N/3.91% | 76.5 N/2.90% | 72.6 N/4.66% | 76.1 N/4.73% |

EXAMPLE 7

Stability Test

The tablets produced with the various rasagiline salts of Example 6 were subjected to stability tests at 60° C. in a closed glass bottle. The results are shown in the following table.

Storage at 60° C. in a closed glass bottle, the portion of decomposed active substance is specified.

| Formulation | Test point | Mesylate | Hydrochloride | Ethane disulfonate | Phosphate | Tartrate |
|---|---|---|---|---|---|---|
| Granulation 1 with mannitol (55%) | initial value | 0.00% | 0.00% | 0.00% | 0.00% | 0.00% |
| | 4 weeks | 2.6% | 2.4% | 1.4% | 3.0% | 3.1% |
| Granulation 2 without | initial value | 0.00% | 0.00% | 0.00% | 0.00% | 0.00% |

-continued

| Formulation | Test point | Mesy-late | Hydro-chloride | Ethane disul-fonate | Phos-phate | Tar-trate |
|---|---|---|---|---|---|---|
| mannitol | 4 weeks | 1.3% | 1.9% | 0.79% | 2.5% | 2.8% |
| Direct compression without mannitol | initial value | 0.00% | 0.00% | 0.00% | 0.00% | 0.00% |
| | 4 weeks | 0.46% | 1.5% | 0.40% | 2.9% | 2.5% |

EXAMPLE 8

Particle Size Distribution

Rasagiline edisilate (rasagiline EDS) was prepared as described in Example 1 and rasagiline oxalate was prepared as in Example 2. The rasagiline tartrate and the rasagiline mesylate were also prepared in analogy to Example 1.

The particle size analyses were carried out by means of laser diffraction in a Malvern Mastersizer 2000 having a Hydro 2000S wet dispersion unit. The plausibility of the results was checked by means of light microscopy using a Leica Z 16 APO.

The principle of the particle size measurement by laser diffraction is based on the fact that the diffraction angle of light at a particle is inversely proportional to the size of the particle. The idealized model of a particle is here spherical since a sphere is the only three-dimensional structure whose size is clearly determined in a two-dimensional projection by a single parameter.

Recognized parameters of the particle size distribution are the values d(0.1), d(0.5) and d(0.9). d(0.1) is the 0.1-quantile of distribution. Correspondingly, 10% (volume weighted) of the particles of a mixture are smaller than the value given for d(0.1). Accordingly, d(0.5) and d(0.9) are the 0.5- and 0.9- quantile, respectively, and thus 50% or 90% of the particles (volume weighted) are smaller than the respectively given value.

All measurements were carried out at a stirring speed of 2500 rpm. The background and measurement times were 10 s each. The sample concentration was chosen such that the attenuation of the laser light (obscuration) was 10 to 20%. Low-viscosity paraffin served as the dispersant.

The following parameters were chosen separately for the different salts:

| Sample | Sonication period [min] | Sonication intensity [%] | Sonication during the measurement | Only red light |
|---|---|---|---|---|
| Rasagiline oxalate | 10 | 30 | no | no |
| Rasagiline tartrate | 2 | 50 | yes | yes |
| Rasagiline EDS | 2 | 30 | no | no |
| Rasagiline mesylate | 5 | 30 | no | no |

Results:
The average values from three measurement cycles±standard deviation (SD) are shown

| Salt | d(0.1) ± SD [μm] | d(0.5) ± SD [μm] | d(0.9) ± SD [μm] | fraction ≦ 250 μm |
|---|---|---|---|---|
| Rasagiline oxalate | 19.9 ± 0.02 | 53.0 ± 0.09 | 120.5 ± 0.66 | 98.1% |
| Rasagiline tartrate | 5.0 ± 0.04 | 40.9 ± 0.57 | 161.2 ± 1.34 | 97.2% |
| Rasagiline EDS | 2.7 ± 0.01 | 12.8 ± 0.08 | 35.1 ± 0.36 | 100.0% |
| Rasagiline mesylate | 13.6 ± 0.05 | 40.5 ± 0.25 | 85.7 ± 0.89 | 100.0% |

The invention claimed is:

1. A salt of rasagiline having an acid of general formula I

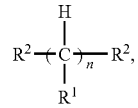

wherein the $R^1$ residues are independently a hydrogen atom or a $C_1$-$C_4$ alkyl residue; the $R^2$ residues are independently a COOH group or an $S(O)_m H$ group, wherein m is the value 2, 3 or 4; and n is an integer ranging from 0 to 4.

2. The salt of rasagiline according to claim 1, wherein all residues $R^1$ represent a hydrogen atom.

3. The salt of rasagiline according to claim 1, wherein n is 0 or 2.

4. The salt of rasagiline according to claim 3, selected from the rasagiline edisilate and the rasagiline oxalate.

5. A medicinal product containing the salt of rasagiline according to claim 1.

6. The medicinal product according to claim 5, formulated as a tablet.

7. A process for stabilizing rasagiline in a medicinal product comprising the step of formulating rasagiline as the salt of rasagiline according to claim 1.

* * * * *